United States Patent
Zhang

(10) Patent No.: US 7,380,985 B2
(45) Date of Patent: Jun. 3, 2008

(54) X-RAY DETECTING APPARATUS AND X-RAY IMAGING APPARATUS

(75) Inventor: Jinglei Zhang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/736,753

(22) Filed: Apr. 18, 2007

(65) Prior Publication Data

US 2007/0248216 A1 Oct. 25, 2007

(30) Foreign Application Priority Data

Apr. 21, 2006 (CN) .................. 2006 1 0074638

(51) Int. Cl.
*H01J 31/50* (2006.01)

(52) U.S. Cl. ...................... 378/189; 378/197

(58) Field of Classification Search ................ 378/19, 378/167–189, 205, 22, 98.8, 197, 204; 250/370.8, 250/370.09
See application file for complete search history.

(56) References Cited

U.S. PATENT DOCUMENTS

| | | | |
|---|---|---|---|
| 5,301,672 A | 4/1994 | Kalender | 600/428 |
| 5,412,562 A | 5/1995 | Nambu et al. | 378/10 |
| 5,684,855 A | 11/1997 | Aradate et al. | 378/4 |
| 5,864,598 A | 1/1999 | Hsieh et al. | 378/4 |
| 6,023,494 A | 2/2000 | Senzig et al. | 378/4 |
| 6,554,472 B1 * | 4/2003 | Dietz et al. | 378/197 |
| 6,683,935 B2 | 1/2004 | Moore | 378/17 |
| 6,979,123 B2 | 12/2005 | Barta et al. | 378/197 |
| 2001/0022833 A1 * | 9/2001 | Kobayashi | 378/177 |
| 2003/0031290 A1 | 2/2003 | Sugihara et al. | |
| 2003/0076920 A1 | 4/2003 | Shinno et al. | |
| 2003/0123603 A1 | 7/2003 | Suzuki | |
| 2004/0208289 A1 | 10/2004 | Barta et al. | |
| 2006/0159229 A1 | 7/2006 | Bowen et al. | |

FOREIGN PATENT DOCUMENTS

| | | |
|---|---|---|
| JP | 10057360 | 3/1998 |
| JP | 2006051234 | 2/2006 |

* cited by examiner

*Primary Examiner*—Courtney Thomas
(74) *Attorney, Agent, or Firm*—Armstrong Teasdale LLP

(57) ABSTRACT

With a view to improving the supporting stability for an X-ray detector, there is provided an X-ray imaging apparatus having an X-ray irradiating apparatus and an X-ray detecting apparatus opposed thereto, the X-ray detecting apparatus comprising an X-ray detector, a support mechanism which supports the X-ray detector through a hinge from a side opposite to an X-ray incidence plane, a shaft connected at one end portion thereof through a hinge to the X-ray detector on the side opposite to the X-ray incidence plane, and a linear actuator adapted to drive an opposite end portion of the shaft in a horizontal direction.

20 Claims, 4 Drawing Sheets

X-RAY DETECTING APPARATUS AND X-RAY IMAGING APPARATUS

CROSS REFERENCE TO RELATED APPLICATIONS

This application claims the benefit of Chinese Patent Application No. 200610074638.5 filed Apr. 21, 2006.

BACKGROUND OF THE INVENTION

The present invention relates to an X-ray detecting apparatus and an X-ray imaging apparatus. Particularly, the present invention is concerned with an X-ray detecting apparatus having an X-ray detector whose direction can be changed, as well as an X-ray imaging apparatus having the X-ray detecting apparatus.

There is known an X-ray detecting apparatus having an X-ray detector whose direction can be changed. In this type of an X-ray detecting apparatus, the X-ray detector is made horizontal when the X-ray irradiating direction is vertical and the X-ray detector is made vertical when the X-ray irradiating direction is horizontal (see, for example, Patent Literature 1).

For supporting an X-ray detector in a cantilevered fashion and for making the direction of the X-ray detector changeable, there is used an X-ray detector supporting mechanism constructed for example as shown in FIG. 4. More specifically, an X-ray detector 100 is attached to a free end portion of a horizontal arm 300 through a hinge 301 and both ends of a linear actuator 500 are connected to the X-ray detector 100 and the arm 300 respectively through hinges 303 and 305. According to such a construction, the X-ray detector 100 can be brought into such a horizontal state as shown in FIG. 4(a) or such a vertical state as shown in FIG. 4(b) with extension or contraction of the linear actuator 500.

[Patent Literature 1] Japanese Published Unexamined Patent Application No. Hei 10(1998)-057360

In the X-ray detecting apparatus of the above construction, the linear actuator 500 is in its most extended state when the X-ray detector 100 is in its horizontal state. In such a state, the linear actuator 500 must bear the load imposed on the X-ray detector 100, but a triangle formed by the hinges 301, 303 and 305 is an obtuse triangle having a large vertex angle centered on the hinge 301, so that a force several times larger than the load on the X-ray detector 100 acts in the axial direction of the linear actuator 500 and hence the supporting stability for the X-ray detector 100 is deteriorated.

SUMMARY OF THE INVENTION

Therefore, it is an object of the present invention to provide an X-ray detecting apparatus superior in the supporting stability for an X-ray detector, as well as an X-ray imaging apparatus provided with such an X-ray detecting apparatus.

In a first aspect of the present invention for solving the above-mentioned problem there is provided an X-ray detecting apparatus comprising an X-ray detector, a support mechanism which supports the X-ray detector through a hinge from a side opposite to an X-ray incidence plane, a shaft connected at one end portion thereof through a hinge to the X-ray detector on the side opposite to the X-ray incidence plane, and a linear actuator adapted to drive an opposite end portion of the shaft in a horizontal direction.

In a second aspect of the present invention for solving the above-mentioned problem there is provided an X-ray imaging apparatus having an X-ray irradiating apparatus and an X-ray detecting apparatus opposed thereto, the X-ray detecting apparatus comprising an X-ray detector, a support mechanism which supports the X-ray detector through a hinge from a side opposite to an X-ray incidence plane, a shaft connected at one end portion thereof through a hinge to the X-ray detector on the side opposite to the X-ray incidence plane, and a linear actuator adapted to drive an opposite end portion of the shaft in a horizontal direction.

For improving the stability of the horizontal movement of the opposite end of the shaft, it is preferable for the X-ray detecting apparatus to further comprise a linear guide to guide the opposite end portion of the shaft so as to move in the horizontal direction.

For supporting the X-ray detector in a cantilevered fashion it is preferable for the support mechanism to be a horizontal arm.

According to the above aspects the present invention, since the X-ray detecting apparatus comprises a support mechanism which supports the X-ray detector through a hinge from the side opposite to the X-ray incidence plane, a shaft connected at one end portion thereof through a hinge to the X-ray detector on the side opposite to the X-ray incidence plane, and a linear actuator adapted to drive the opposite end portion of the shaft in a horizontal direction, the X-ray detecting apparatus is superior in the supporting stability for the X-ray detector and it is possible to implement an X-ray imaging apparatus provided with such an X-ray detecting apparatus.

Further objects and advantages of the present invention will be apparent from the following description of the preferred embodiments of the invention as illustrated in the accompanying drawings.

DETAILED DESCRIPTION OF THE INVENTION

Figure 1:
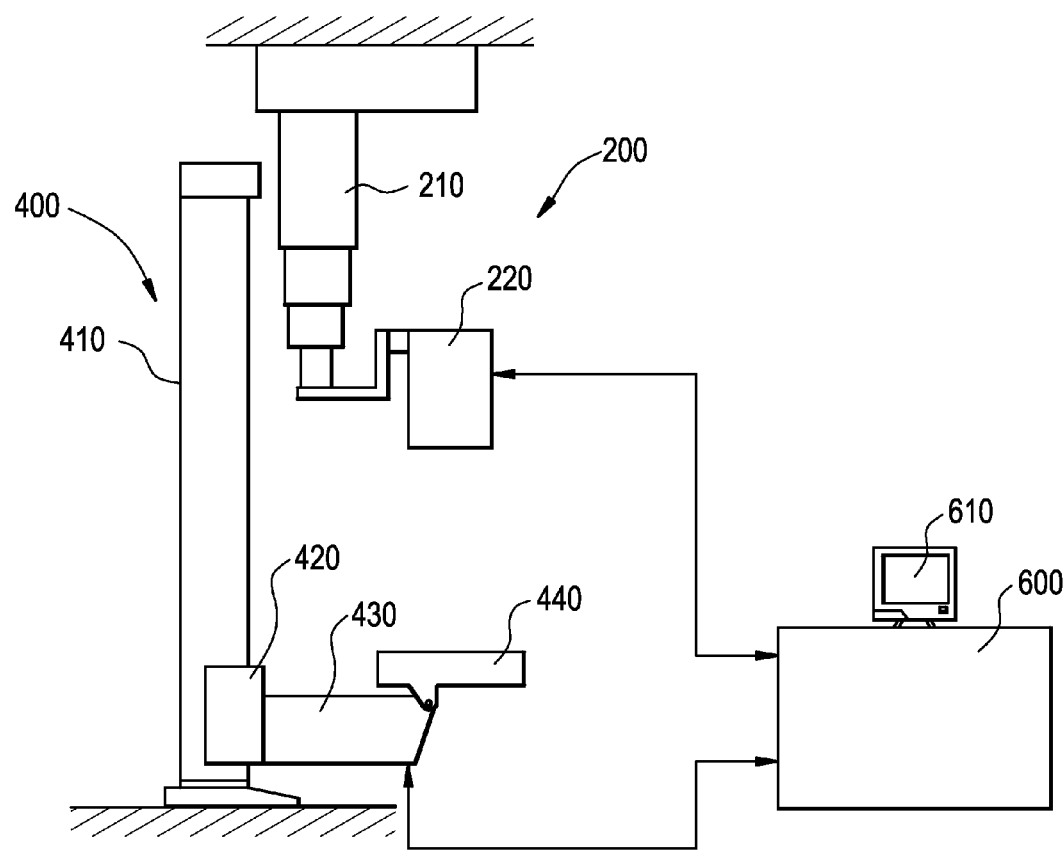
FIG. 1 illustrates the construction of an X-ray imaging apparatus as an example of the best mode for carrying out the present invention.

The best mode for carrying out the present invention will be described in detail hereinunder with reference to the drawings. The present invention is not limited to the best mode for carrying out the invention. FIG. 1 shows a schematic construction of an X-ray imaging apparatus. This system is an example of the best mode for carrying out the present invention. By the construction of this system there is shown an example of the best mode for carrying out the invention related to the X-ray imaging apparatus. Further, by a part of the construction of this system there is shown an example of the best mode for carrying out the invention related to the X-ray detecting apparatus.

As shown in FIG. 1, this system has an X-ray irradiating apparatus 200 and an X-ray detecting apparatus 400. The X-ray irradiating apparatus 200 is an example of the X-ray irradiating apparatus according to the present invention and the X-ray detecting apparatus 400 is an example of the X-ray detecting apparatus according to the present invention.

The X-ray irradiating apparatus 200 includes an X-ray source 220 attached to a lower end of a column 210 suspended from a ceiling. The X-ray source 220 is constructed so that its direction is changeable to change the X-ray irradiating direction. The column 210 which supports the X-ray source 220 can extend and contract in its longitudinal direction and is movable horizontally along the ceiling.

The X-ray detecting apparatus 400 includes a carriage 420 attached vertically movably to a column 410 which is erected from a floor, an arm 430 attached horizontally to the carriage 420, and an X-ray detector 440 attached to a free end of the arm 430.

The X-ray detector 440 is a flat plate-like structure and has a light receiving surface whose inclination is changeable so as to become horizontal or vertical in accordance with the direction of incidence of X-ray. The X-ray detector 440 is an example of the X-ray detector according to the present invention. The arm 430 is an example of the support mechanism defined in the present invention and is also an example of the arm defined in the present invention. Since the X-ray detector 440 is supported by the horizontal arm, it can be supported in a cantilevered fashion.

A signal detected by the X-ray detector 440 is inputted to an operator console 600. The operator console 600 reconstructs a radioscopic image of an object to be radiographed in accordance with the signal inputted from the X-ray detector 440 and displays it on a display 610. The X-ray detector 440 may be a photosensitive material which is sensitized with X-ray. In this case, the radioscopic image is made visible by a developing treatment.

Under operation by an operator, the operator console 600 controls both the X-ray irradiating apparatus 200 and the X-ray detecting apparatus 400. For the X-ray irradiating apparatus 200, the operator console 600 controls horizontal and vertical positions of the X-ray source 220 and an X-ray irradiating direction, and further controls the intensity of X-ray and an irradiation timing. For the X-ray detector 400 the operator console 600 controls the height of the X-ray detector 440 in accordance with the vertical position of the X-ray source 220 and also controls the inclination of the light receiving surface so that it becomes horizontal or vertical in accordance with the X-ray irradiating direction.

Figure 2A:
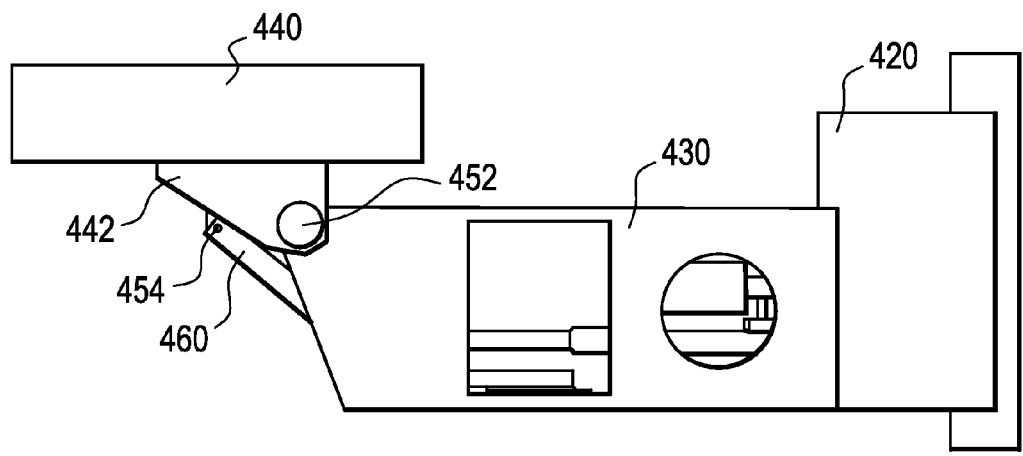
FIGS. 2a and 2b illustrate the constructions of an X-ray detecting apparatus as another example of the best mode for carrying out the present invention.
Figure 2B:
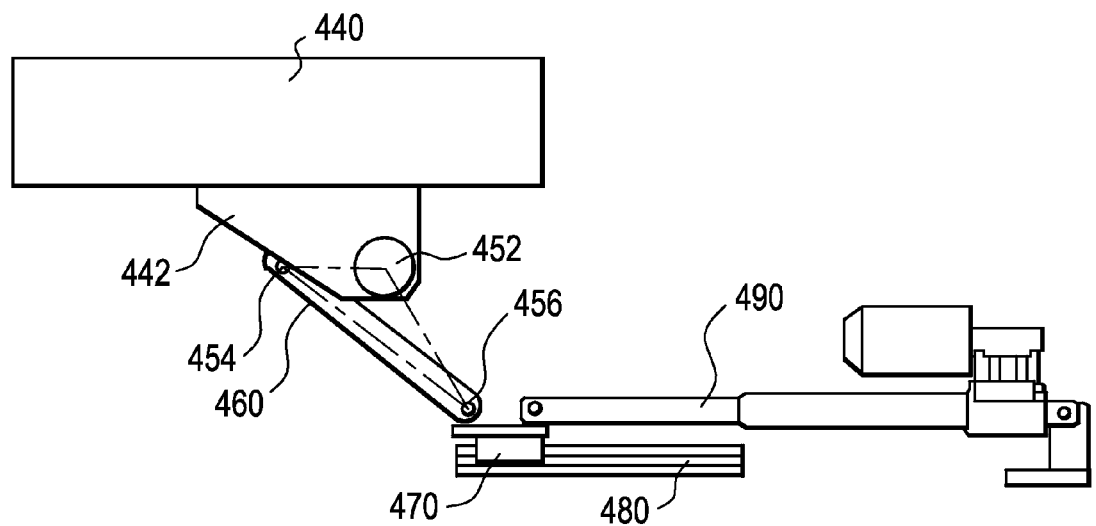
Figure 3A:
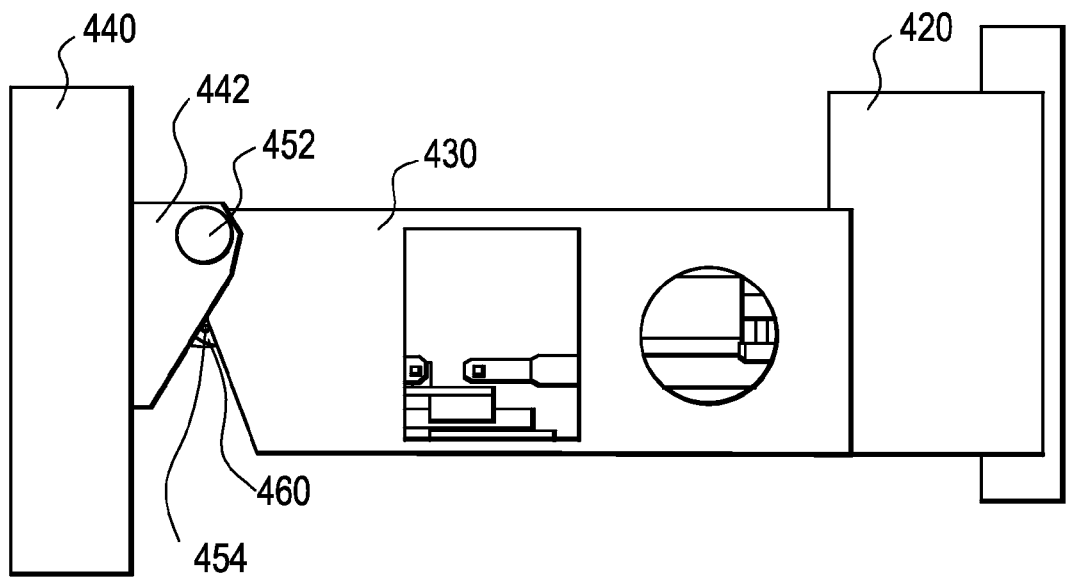
FIGS. 3a and 3b illustrate the constructions of the X-ray detecting apparatus as another example of the best mode for carrying out the present invention.
Figure 3B:
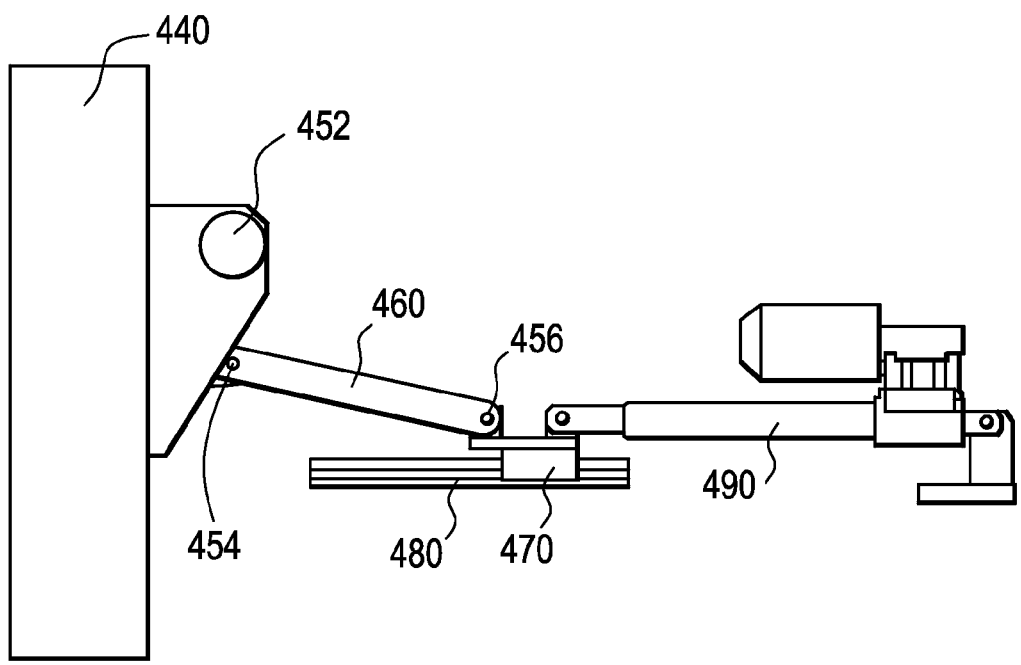

The arm 430 incorporates a drive mechanism for the X-ray detector 440. The following description is now provided about the drive mechanism for the X-ray detector 440. The construction of the drive mechanism is shown in FIGS. 2 and 3. FIG. 2 show states in which the X-ray detector 440 has been actuated to a horizontal state, while FIG. 3 show states in which the X-ray detector 440 has been actuated to a vertical state. In FIGS. 2 and 3, (a) show states including the carriage 420 and the arm 430, while (b) shows states in which they are omitted.

As shown in FIGS. 2 and 3, the X-ray detector 440 has a bracket 442 on the side opposite to the light receiving surface, the bracket 442 being attached to an end portion of the arm 430 through a hinge 452.

One end of a shaft 460 is connected to the bracket 442 through a hinge 454. An opposite end of the shaft 460 is connected to a slider 470 through a hinge 456. The shaft 460 is an example of the shaft defined in the present invention.

The slider 470 is movable horizontally along a linear guide 480. A working end of a linear actuator 490 is connected to the slider 470. The linear actuator 490 is an example of the linear actuator defined in the present invention. The linear guide 480 is an example of the linear guide defined in the present invention. With the linear guide 480, it is possible to improve the stability of the horizontal movement at the opposite end of the shaft 460.

In FIG. 2 the slider 470 is in a state of having been moved near to the left end of the linear guide 480 by being pushed by the linear actuator 490. At this time, the X-ray detector 440 is pushed by the shaft 460 and thereby rotates clockwise about the hinge 452, so that the light receiving surface thereof is in a horizontal state.

In FIG. 3 the slider 470 is in a state of having been pulled back by the linear actuator 490 and moved near to the right end of the linear guide 480. At this time, the X-ray detector 440 is pulled by the shaft 460 and thereby rotates counterclockwise about the hinge 452, so that the light receiving surface thereof is in a vertical state.

Figure 4A:
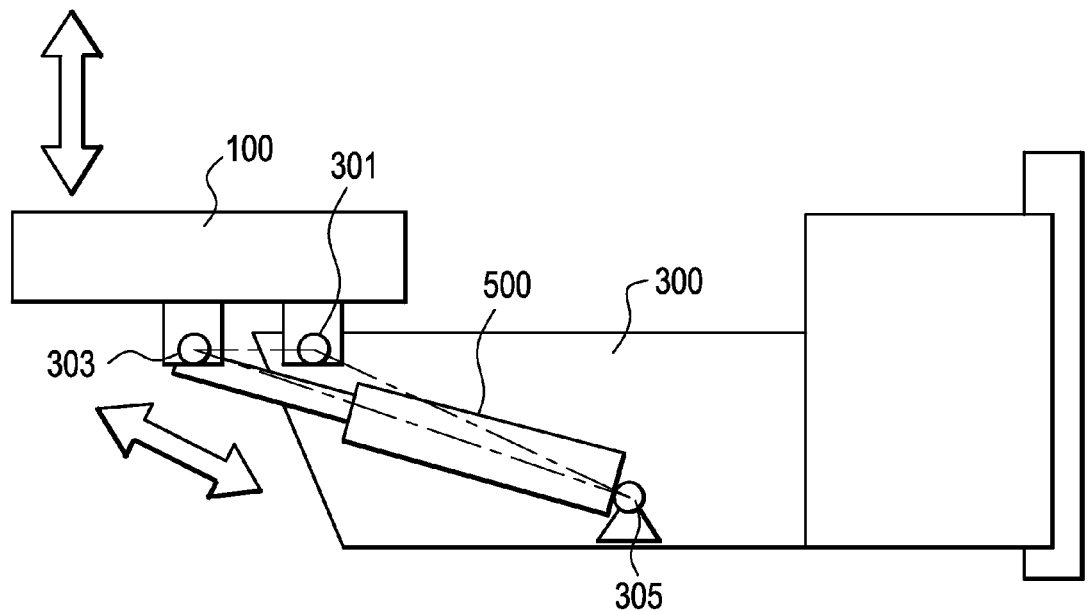
FIGS. 4a and 4b illustrate the constructions of a conventional X-ray detecting apparatus.
Figure 4B:
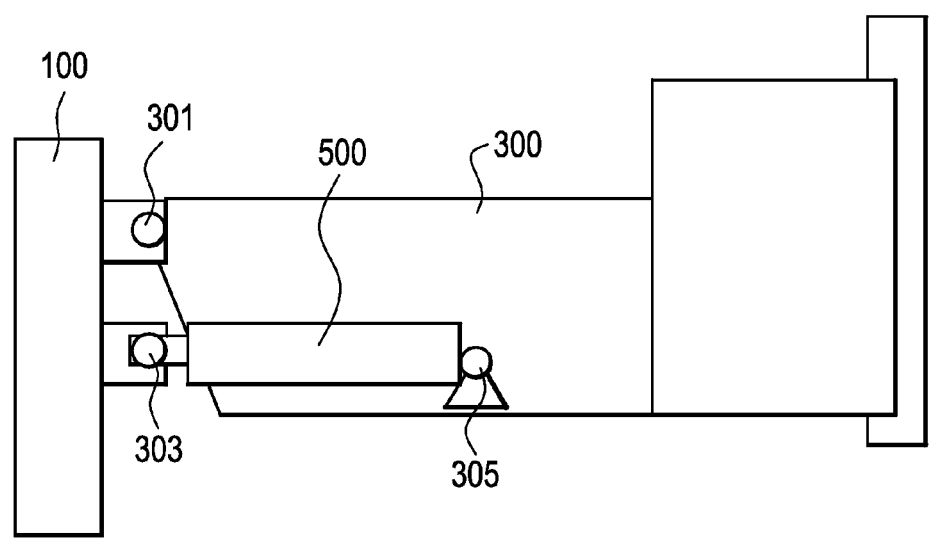

With the X-ray detector 440 horizontal as shown in FIG. 2, a vertex angle centered on the hinge 452 of the triangle formed by the hinges 452, 454 and 456 is smaller than in the conventional construction shown in FIG. 4. Consequently, when the load imposed on the X-ray detector 440 is the same, the force acting in the axial direction of the shaft 460 is smaller than in the conventional construction. As a result, the supporting stability for the X-ray detector 440 is improved.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray detecting apparatus comprising;
   an X-ray detector;
   a support mechanism for supporting said X-ray detector, said support mechanism comprising a first hinge coupled to a first side of said X-ray detector opposite to an X-ray incidence plane of said X-ray detector, said first hinge providing a rotation axis for rotating said X-ray detector to change a facing direction of the X-ray incidence plane;
   a shaft connected at a first end portion thereof using a second hinge to couple said X-ray detector on said first side opposite to the X-ray incidence plane; and
   a linear actuator coupled to an opposite second end portion of said shaft for driving said second end portion in a horizontal direction when rotating said X-ray detector.

2. An X-ray detecting apparatus according to claim 1, further comprising a linear guide for guiding said second end portion of said shaft so as to move in the horizontal direction.

3. An X-ray detecting apparatus according to claim 1, wherein said support mechanism comprises a horizontal arm.

4. An X-ray detecting apparatus according to claim 2, wherein said support mechanism comprises a horizontal arm.

5. An X-ray imaging apparatus having an X-ray irradiating apparatus and an X-ray detecting apparatus opposed thereto, said X-ray detecting apparatus comprising:
   an X-ray detector;
   a support mechanism for supporting said X-ray detector, said support mechanism comprising a first hinge coupled to a first side of said X-ray detector opposite to an X-ray incidence plane of said X-ray detector, said first hinge providing a rotation axis for rotating said X-ray detector in order to change a facing direction of the X-ray incidence plane;

a shaft connected at a first end portion thereof using a second hinge to couple said X-ray detector on said first side opposite to the X-ray incidence plane; and a linear actuator coupled to an opposite second end portion of said shaft for driving said second end portion in a horizontal direction when rotating said X-ray detector.

6. An X-ray imaging apparatus according to claim 5, wherein said X-ray detecting apparatus further comprises a linear guide for guiding said second end portion of said shaft so as to move in the horizontal direction.

7. An X-ray imaging apparatus according to claim 5, wherein said support mechanism comprises a horizontal arm.

8. An X-ray imaging apparatus according to claim 6, wherein said support mechanism comprises a horizontal arm.

9. An X-ray imaging apparatus comprising:

an X-ray irradiating apparatus configured to move in a vertical and a horizontal direction;

an X-ray detector; and a liner actuator coupled to said X-ray detector and configured to move said X-ray detector from a vertical position to a horizontal position, said linear actuator is only moveable in a single plane of travel.

10. An X-ray imaging apparatus in accordance with claim 9, wherein said linear actuator is configured to move in only a horizontal plane of travel.

11. An X-ray imaging apparatus in accordance with claim 9, wherein said linear actuator is configured to move said X-ray detector to a substantially vertical position when said linear actuator is fully retracted and to move said X-ray detector to a substantially horizontal position when said linear actuator is fully extended.

12. An X-ray imaging apparatus in accordance with claim 9, further comprising:

a shaft coupled to said X-ray detector; and a slider coupled betweens said shaft and said linear actuator, said slider and said linear actuator each configured to move in the same plane of travel.

13. An X-ray imaging apparatus in accordance with claim 12, further comprising a linear guide coupled to said slider, said linear guide configured to restrict the movement of said slider to the single plane of travel.

14. An X-ray imaging apparatus in accordance with claim 12, further comprising a hinge coupled between said shaft and said detector, said hinge configured to support said X-ray detector on a side opposite to an X-ray incidence plane.

15. An X-ray imaging apparatus in accordance with claim 9, wherein said linear actuator and said slider are each configured to move in a horizontal plane of travel.

16. An X-ray imaging apparatus in accordance with claim 9, further comprising:

a column coupled to a floor;

a carriage coupled to said column, said carriage is configured to move said X-ray detector in a vertical direction.

17. An X-ray imaging apparatus in accordance with claim 15 further comprising an arm coupled between said carriage and said X-ray detector such that said X-ray detector is cantilevered from said column.

18. An X-ray imaging apparatus in accordance with claim 17, further comprising a bracket coupled to said X-ray detector, said bracket is disposed on a side opposite to a light receiving surface of said detector, said bracket is attached to an end portion of said arm using said hinge.

19. An X-ray imaging apparatus in accordance with claim 17, further comprising a first hinge utilized to coupled said shaft to said bracket and a second hinge utilized to couple said shaft to said slider.

20. An X-ray imaging apparatus in accordance with claim 9, wherein said X-ray irradiating apparatus is coupled to a column and said column is coupled to a ceiling.

* * * * *